(12) United States Patent
Pratt et al.

(10) Patent No.: US 10,532,137 B2
(45) Date of Patent: Jan. 14, 2020

(54) NEGATIVE PRESSURE THERAPY WITH DYNAMIC PROFILE CAPABILITY

(71) Applicant: KCI Licensing, Inc., San Antonio, TX (US)

(72) Inventors: Benjamin Andrew Pratt, Poole (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 339 days.

(21) Appl. No.: 15/495,151

(22) Filed: Apr. 24, 2017

(65) Prior Publication Data
US 2017/0224892 A1  Aug. 10, 2017

Related U.S. Application Data

(62) Division of application No. 14/186,534, filed on Feb. 21, 2014, now Pat. No. 9,662,429.
(Continued)

(51) Int. Cl.
*A61M 1/00* (2006.01)
*A61F 13/02* (2006.01)
(Continued)

(52) U.S. Cl.
CPC ..... *A61M 1/0088* (2013.01); *A61F 13/00068* (2013.01); *A61F 13/0206* (2013.01);
(Continued)

(58) Field of Classification Search
CPC ............ A61F 13/00068; A61F 13/0206; A61F 13/0216; A61F 2013/0017;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

(Continued)

*Primary Examiner* — Adam Marcetich

(57) ABSTRACT

An apparatus and system for fluidly connecting a reduced-pressure source to a dressing and a method for manufacturing and using the same include a base having an aperture and a wall having a peripheral portion coupled to the base. The wall may form a cavity in fluid communication with the aperture. The apparatus also may include a conduit port fluidly coupled to the cavity and adapted to receive a conduit. The base may be adapted to couple to the dressing, and the wall may be adapted to collapse from a first position to a second position in response to a supply of reduced pressure from the reduced-pressure source.

27 Claims, 5 Drawing Sheets

Related U.S. Application Data

(60) Provisional application No. 61/784,797, filed on Mar. 14, 2013.

(51) Int. Cl.
  *A61F 13/00* (2006.01)
  *A61M 39/10* (2006.01)
  *A61M 39/12* (2006.01)

(52) U.S. Cl.
  CPC ......... *A61F 13/0216* (2013.01); *A61M 1/009* (2014.02); *A61M 1/0023* (2013.01); *A61M 1/0027* (2014.02); *A61M 1/0031* (2013.01); *A61M 1/0066* (2013.01); *A61M 1/0084* (2013.01); *A61M 1/0086* (2014.02); *A61M 1/0096* (2014.02); *A61M 39/1011* (2013.01); *A61M 39/12* (2013.01); *A61F 2013/0017* (2013.01); *A61F 2013/00174* (2013.01); *A61M 1/0009* (2013.01); *A61M 2205/18* (2013.01); *A61M 2205/3344* (2013.01); *A61M 2205/52* (2013.01); *A61M 2205/7536* (2013.01); *A61M 2207/00* (2013.01); *Y10T 156/10* (2015.01)

(58) Field of Classification Search
  CPC ....... A61F 2013/00174; A61M 1/0009; A61M 1/0023; A61M 1/0027; A61M 1/0031; A61M 1/0066; A61M 1/0084; A61M 1/0086; A61M 1/0088; A61M 1/009; A61M 1/0096; A61M 2205/18; A61M 2205/3344; A61M 2205/52; A61M 2205/7536; A61M 2207/00; A61M 39/1011; A61M 39/12; Y10T 156/10
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,824,145 A | 4/1989 | Carlsson |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A * | 8/1996 | Gross .................. A61M 1/0088 604/313 |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,003,906 A | 12/1999 | Fogarty et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,701,890 B1 | 3/2004 | Suhre et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |

(56) References Cited

U.S. PATENT DOCUMENTS

| | | | |
|---|---|---|---|
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0161332 | A1 | 10/2002 | Ramey |
| 2004/0064132 | A1* | 4/2004 | Boehringer .......... A61M 1/0011 604/543 |
| 2005/0245899 | A1 | 11/2005 | Swisher |
| 2005/0261642 | A1 | 11/2005 | Weston |
| 2006/0100594 | A1* | 5/2006 | Adams ............... A61M 1/0088 604/313 |
| 2006/0271015 | A1 | 11/2006 | Mantell |
| 2007/0023051 | A1* | 2/2007 | Cook ................. A61M 16/044 128/207.15 |
| 2007/0156117 | A1 | 7/2007 | Adams et al. |
| 2007/0265585 | A1 | 11/2007 | Joshi et al. |
| 2008/0306456 | A1* | 12/2008 | Riesinger ............ A61F 13/0203 604/316 |
| 2009/0110777 | A1 | 4/2009 | Buisson |
| 2009/0234309 | A1 | 9/2009 | Vitaris et al. |
| 2009/0299255 | A1 | 12/2009 | Kazala, Jr. et al. |
| 2009/0299303 | A1 | 12/2009 | Seegert |
| 2009/0312727 | A1* | 12/2009 | Heaton ................ A61M 1/008 604/318 |
| 2010/0137775 | A1 | 6/2010 | Hu et al. |
| 2010/0262095 | A1* | 10/2010 | Hall ................... A61M 1/0084 604/319 |
| 2010/0280469 | A1* | 11/2010 | Hall ................... A61M 1/0088 604/319 |
| 2010/0324510 | A1 | 12/2010 | Andresen et al. |
| 2011/0054365 | A1 | 3/2011 | Greener |
| 2011/0066178 | A1 | 3/2011 | Blin |
| 2011/0092927 | A1 | 4/2011 | Wilkes et al. |
| 2011/0121558 | A1 | 5/2011 | Kanner |
| 2011/0224633 | A1 | 9/2011 | Robinson et al. |
| 2011/0275964 | A1* | 11/2011 | Greener ............ A61M 1/0031 601/6 |
| 2011/0276016 | A1 | 11/2011 | Tsai |
| 2011/0282309 | A1 | 11/2011 | Adie et al. |
| 2011/0295236 | A1* | 12/2011 | Gregory ............ A61M 3/0295 604/540 |
| 2012/0016324 | A1* | 1/2012 | Long .................. A61M 1/0088 604/319 |
| 2012/0041425 | A1 | 2/2012 | Tsunematsu et al. |
| 2013/0030394 | A1 | 1/2013 | Locke et al. |
| 2013/0041351 | A1 | 2/2013 | Shahim |
| 2014/0052063 | A1* | 2/2014 | Gregory .......... A61M 25/10187 604/99.03 |
| 2014/0163491 | A1 | 6/2014 | Schuessler et al. |
| 2014/0350494 | A1 | 11/2014 | Hartwell et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2014066057 A1 | 5/2014 |

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, YU. A., et al; "Vacuum Therapy in the Treatment of Purulent Lactation Mastitis"; Vestnik Khirurgi, May 14, 1986, pp. 66-70, and 9 page English translation thereof.

Yusupov. YU.N., et al; "Active Wound Drainage", Vestnki Khirurgi, vol. 138, Issue 4, 1987, and 7 page English translation thereof.

Davydov, YU.A., et al; "Bacteriological and Cytological Assessment of Vacuum Therapy for Purulent Wounds"; Vestnik Khirugi, Oct. 1988, pp. 48-52, and 8 page English translation thereof.

Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

(56) References Cited

OTHER PUBLICATIONS

Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for corresponding PCT/US2014/017740 dated Jun. 11, 2014.
Nave; Carl Rod. Hyperphysics: Poiseuille's Law, 2012. http://hyperphysics.phy-astr.gsu.edu/hbase/ppois.html. Department of Physics and Astronomy, Georgia State University. Accessed Feb. 21, 2017.

* cited by examiner

NEGATIVE PRESSURE THERAPY WITH DYNAMIC PROFILE CAPABILITY

This application is a divisional of U.S. patent application Ser. No. 14/186,534, filed Feb. 21, 2014, which claims benefit, under 35 U.S.C. § 119(e), of the filing of U.S. Provisional Patent Application No. 61/784,797 filed Mar. 14, 2013, entitled "Negative Pressure Therapy with Dynamic Profile Capability," the disclosure of which is hereby incorporated by reference in its entirety.

TECHNICAL FIELD

The present disclosure relates generally to systems, apparatuses, and methods for providing negative pressure therapy to a tissue site. More particularly, but not by way of limitation, the present disclosure relates to a dressing connector having a dynamic profile.

BACKGROUND

Clinical studies and practice have shown that reducing pressure in proximity to a tissue site can augment and accelerate growth of new tissue at the tissue site. The applications of this phenomenon are numerous, but is has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the profile of a dressing can be a limiting factor in its application to some tissue sites. For example, many dressings are coupled to a reduced-pressure source through a connection pad. The profile of a dressing and connection pad can cause significant discomfort or secondary damage to a tissue site if the tissue site bears any weight of a patient, such as on a foot, a sacrum, or the back of a bed-ridden patient. Thus, the development and operation of reduced-pressure systems, components, and processes continues to present significant challenges to manufacturers, healthcare providers, and patients.

SUMMARY

According to an illustrative exemplary embodiment, an apparatus for fluidly connecting a reduced-pressure source to a dressing is described. The apparatus may include a base having an aperture and a wall having a peripheral portion coupled to the base. The wall forms a cavity in fluid communication with the aperture. The apparatus also may include a conduit port fluidly coupled to the cavity and adapted to receive a conduit. The base may be adapted to couple to the dressing, and the wall may be adapted to collapse from a first position to a second position in response to a supply of reduced pressure from the reduced-pressure source.

According to another illustrative exemplary embodiment, a system for treating a tissue site with reduced pressure is described. The system may include a manifold adapted to be placed proximate to the tissue site and a sealing member adapted to cover the manifold and a portion of intact epidermis to form a sealed space. The system also may include a reduced-pressure source adapted to supply reduced pressure to the manifold and a connector adapted to fluidly couple the reduced pressure source to the manifold through the sealing member. The connector may include a wall forming a cavity. The wall may be adapted to transition between a first position and a second position in response to a supply of reduced pressure. The connector also may include a conduit port adapted to fluidly couple the cavity to a conduit. The connector further may include a base extending from a peripheral portion of the wall and adapted to be coupled to the sealing member.

According to yet another illustrative exemplary embodiment, a method of manufacturing an apparatus for fluidly connecting a reduced-pressure source to a dressing is described. A base having an aperture may be formed and a wall having a peripheral portion may be coupled to the base. The wall may form a cavity in fluid communication with the aperture. A conduit port may be fluidly coupled to the cavity. The conduit port may be adapted to receive a conduit. The base may be adapted to couple to the dressing, and the wall may be adapted to collapse from a first position to a second position in response to a supply of reduced pressure from the reduced-pressure source.

According to still another embodiment, a method of treating a tissue site with reduced pressure is described. A manifold may be disposed proximate to the tissue site, and a sealing member may be secured over the manifold and a portion of intact epidermis to form a sealed space. The sealing member may have an opening formed therein. A connector may be coupled to the sealing member proximate to the opening. A reduced-pressure source may be fluidly coupled to the connector to supply reduced pressure to the manifold. The connector may include a base having an aperture and a wall having a peripheral portion coupled to the base. The wall may form a cavity in fluid communication with the aperture. The connector may further include a conduit port fluidly coupled to the cavity and adapted to receive a conduit. The wall may be adapted to collapse from a first position to a second position in response to a supply of reduced pressure from the reduced-pressure source. Reduced pressure may be supplied to the manifold through the connector. At least a portion of the wall may be collapsed from the first position to the second position when a therapeutic reduced pressure may be reached in the sealed space.

Other aspects, features, and advantages of the illustrative exemplary embodiments will become apparent with reference to the drawings and detailed description that follow.

DETAILED DESCRIPTION OF ILLUSTRATIVE EXEMPLARY EMBODIMENTS

New and useful systems, methods, and apparatuses for supplying reduced-pressure to a tissue site with a low profile dressing are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. Reference to "an" item refers to one or more of those items. The claimed subject matter may also encompass alternative exemplary embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
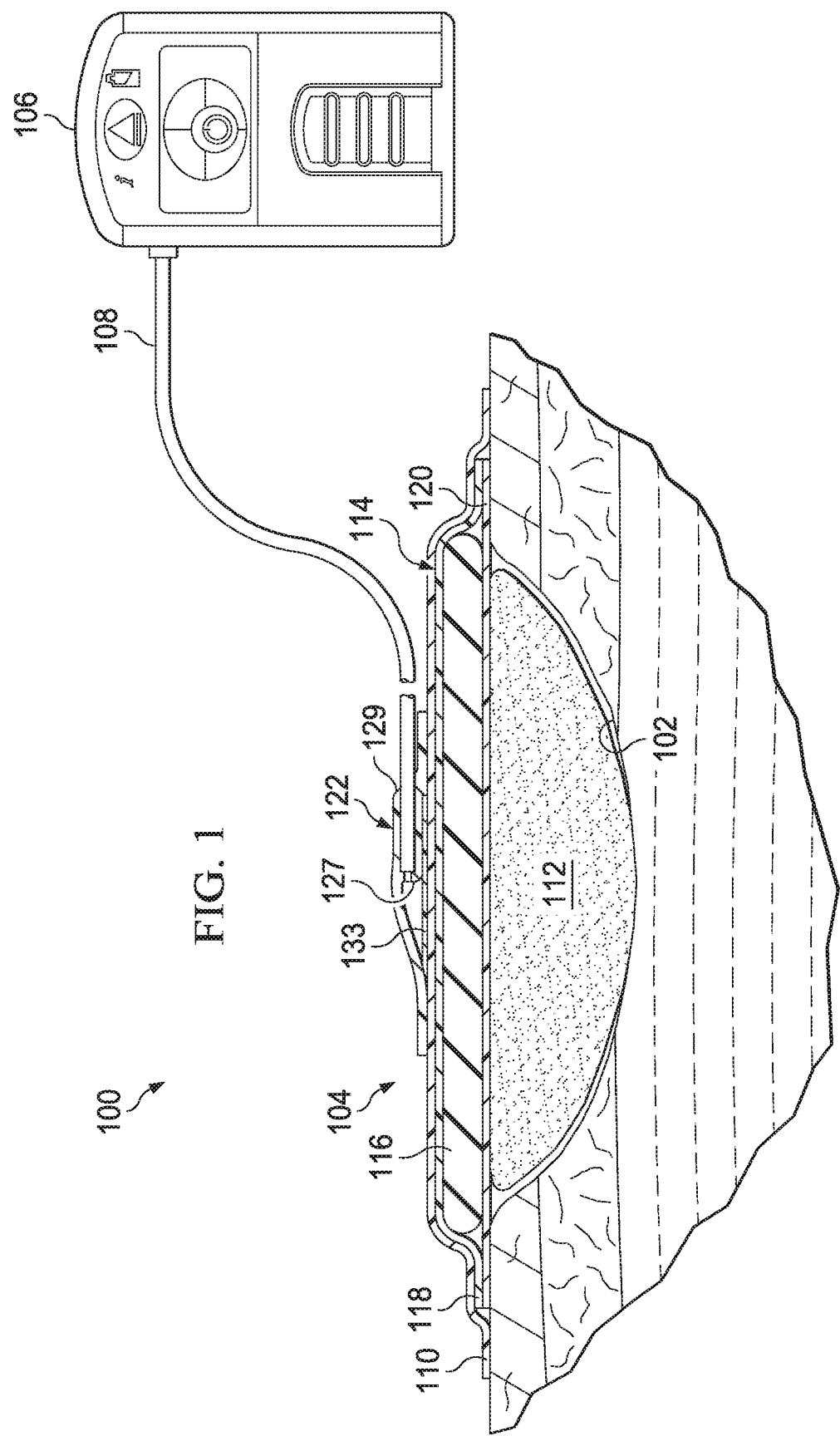
FIG. 1 is a sectional view of a reduced-pressure system for application of reduced pressure to a tissue site.

FIG. 1 is a sectional view of one exemplary embodiment of a therapy system 100 for supplying reduced pressure to a tissue site 102 having a low profile in accordance with this specification. As illustrated, the therapy system 100 may include a dressing 104 fluidly coupled to a reduced-pressure source 106. A regulator or controller may also be fluidly coupled to the dressing 104 and the reduced-pressure source 106.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluid flow toward lower pressure along a fluid path. This orientation may generally be presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications (such as by substituting a positive-pressure source for a reduced-pressure source) and this descriptive convention should not be construed as a limiting convention.

A reduced-pressure source, such as the reduced-pressure source 106, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

In general, components of the therapy system 100 may be coupled directly or indirectly. For example, reduced-pressure source 106 may be directly coupled to the regulator and indirectly coupled to the dressing 104 through the regulator. Components may be fluidly coupled to each other to provide a path for transferring fluid (i.e., liquid and/or gas) between the components. In some exemplary embodiments, components may be fluidly coupled with a tube 108, for example. A "tube," as used herein, broadly refers to a tube, pipe, hose, conduit, or other structure with one or more lumina adapted to convey fluid between two ends. Typically, a tube is an elongated, cylindrical structure with some flexibility, but the geometry and rigidity may vary. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The dressing 104 generally may include a cover, such as a drape 110, and a tissue interface, such as a manifold 112. The drape 110 may be an example of a sealing member. A sealing member may be constructed from a material that can provide a fluid seal between two components or two environments, such as between a therapeutic environment and a local external environment. The sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained to create a sealed therapeutic environment. An attachment device may be used to attach a sealing member to an attachment surface, such as an undamaged epidermis, a gasket, or another sealing member. The attachment device may take many forms. For example, an attachment device may be a medically acceptable, pressure-sensitive adhesive that extends about a periphery, a portion of, or an entirety of the sealing member. Other exemplary embodiments of an attachment device may include a double-sided tape, paste, hydrocolloid, hydrogel, silicone gel, organogel, or an acrylic adhesive.

The manifold 112 can be generally adapted to contact the tissue site 102. The manifold may be partially or fully in contact with the tissue site 102. If the tissue site 102 is a wound, for example, the manifold 112 may partially or completely fill the wound, or may be placed over the wound. The manifold 112 may take many forms, and may have many sizes, shapes, or thicknesses depending on a variety of factors, such as the type of treatment being implemented or the nature and size of the tissue site 102. For example, the size and shape of the manifold 112 may be adapted to the contours of deep and irregular shaped tissue sites.

More generally, a manifold may be a substance or structure adapted to distribute reduced pressure across a tissue site, remove fluid from a tissue site, or both. In some exemplary embodiments, though, a manifold may also facilitate delivering fluid across a tissue site, if the fluid path is reversed or a secondary fluid path is provided, for example. A manifold may include flow channels or pathways that distribute fluid provided to and removed from a tissue site around the manifold. In one exemplary embodiment, the flow channels or pathways may be interconnected to improve distribution of fluid provided to or removed from a tissue site. For example, cellular foam, open-cell foam, porous tissue collections, and other porous material, such as gauze or felted mat, generally include structural elements arranged to form flow channels. Liquids, gels, and other foams may also include or be cured to include flow channels.

In one exemplary embodiment, the manifold 112 may be a porous foam material having interconnected cells or pores adapted to uniformly (or quasi-uniformly) distribute reduced pressure to the tissue site 102. The foam material may be either hydrophobic or hydrophilic. In one non-limiting example, the manifold 112 can be an open-cell, reticulated polyurethane foam such as GranuFoam® dressing available from Kinetic Concepts, Inc. of San Antonio, Tex.

In an example in which the manifold 112 may be made from a hydrophilic material, the manifold 112 may also wick fluid away from the tissue site 102, while continuing to distribute reduced pressure to the tissue site 102. The wicking properties of the manifold 112 may draw fluid away from the tissue site 102 by capillary flow or other wicking mechanisms. An example of a hydrophilic foam may be a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 112 may further promote granulation at the tissue site 102 when pressure within the sealed therapeutic environment is reduced. For example, any or all of the surfaces of the manifold 112 may have an uneven, coarse, or jagged profile that can induce microstrains and stresses at the tissue site 102 if reduced pressure is applied through the manifold 112.

In one exemplary embodiment, the manifold may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 112 may further serve as a scaffold for new cell-growth, or a scaffold material may be used in conjunction with the manifold 112 to promote cell-growth. A scaffold may generally be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In operation, the manifold 112 may be placed within, over, on, or otherwise proximate to a tissue site, for example the tissue site 102. The drape 110 may be placed over the manifold 112 and sealed to tissue proximate to the tissue site 102. The tissue proximate to the tissue site 102 may often be undamaged epidermis peripheral to the tissue site 102. Thus, the dressing 104 can provide the sealed therapeutic environment proximate to the tissue site 102, substantially isolated from the external environment, and the reduced-pressure source 106 can reduce the pressure in the sealed therapeutic environment. An opening may be formed in the drape 110 so that the reduced pressure source 106 may be fluidly coupled to the sealed therapeutic environment. Reduced pressure applied uniformly through the manifold 112 in the sealed therapeutic environment can induce macrostrain and microstrain in the tissue site 102, as well as remove exudates and other fluid from the tissue site 102, which can be collected in the container 112 and disposed of properly. In an exemplary embodiment, a filter 133 may be disposed proximate to the opening to limit movement of liquid out of the sealed therapeutic environment.

"Reduced pressure" generally refers to a pressure less than a local ambient pressure, such as the ambient pressure in a local environment external to a sealed therapeutic environment provided by the dressing 104. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The therapy system 100 may also include a container 114. The container 114 may be representative of a container, canister, pouch, or other storage component that can be used to manage exudates and other fluid withdrawn from a tissue site. In many environments, a rigid container may be preferred or required for collecting, storing, and disposing of fluid. In other environments, fluid may be properly disposed of without rigid container storage, and a re-usable container could reduce waste and costs associated with reduced-pressure therapy. In an exemplary embodiment, the container 114 may include an absorbent member 116, a first layer, such as a downstream layer 118, and a second layer, such as an upstream layer 120. The upstream layer 120 and the downstream layer 118 envelop or enclose the absorbent member 116, which can absorb body fluid drawn by the reduced pressure through the upstream layer 120.

The absorbent member 116 may be formed of or include an absorbent material. The absorbent material can hold, stabilize, and/or solidify fluid that may be collected from the tissue site 102. The absorbent material may be of the type referred to as "hydrogels," "super-absorbents," or "hydrocolloids." When disposed within the dressing 104, the absorbent material may be formed into fibers or spheres to manifold reduced pressure until the absorbent member 116 becomes saturated. Spaces or voids between the fibers or spheres may allow a reduced pressure that is supplied to the dressing 104 to be transferred within and through the absorbent member 116 to the manifold 112 and the tissue site 102. In some exemplary embodiments, the absorbent material may be Texsus FP2325 having a material density of 800 grams per square meter (gsm). In other exemplary embodiments, the absorbent material may be BASF 402C, TAL 2317 available from Technical Absorbents Limited, sodium polyacrylate super absorbers, cellulosics (carboxy methyl cellulose and salts such as sodium CMC), or alginates.

In some exemplary embodiments, the upstream layer 120 and the downstream layer 118 have perimeter dimensions that are larger than the perimeter dimensions of the absorbent member 116. When the absorbent member 116 is positioned between the upstream layer 120 and the downstream layer 118 and the center portions of the absorbent member 116, the upstream layer 120 and the downstream layer 118 are aligned, the upstream layer 120 and the downstream layer 118 extend beyond the perimeter of the absorbent member 116. In some exemplary embodiments, the upstream layer 120, and the downstream layer 118 surround the absorbent member 116. Peripheral portions of the upstream layer 120 and the downstream layer 118 are coupled so that the upstream layer 120 and the downstream layer 118 enclose the absorbent member 116. The upstream layer 120 and the downstream layer 118 may be coupled by high frequency welding, ultrasonic welding, heat welding, or impulse welding, for example. In other exemplary embodiments, the upstream layer 120 and the downstream layer 118 may be coupled by bonding or folding, for example.

The upstream layer 120 and the downstream layer 118 may each have a first side and a second side. In some exemplary embodiments, the first side and the second side may have different relative liquid affinities so that one side may be considered hydrophilic and the other side may be considered hydrophobic. The upstream layer 120 and the downstream layer 118 may be formed of non-woven material having a thickness. In some exemplary embodiments, the upstream layer 120 and the downstream layer 118 have a polyester fibrous porous structure. The upstream layer 120 and the downstream layer 118 may preferably be non-perforated. The upstream layer 120 and the downstream layer 118 may be formed of Libeltex TDL2 or TL4, for example.

The hydrophobic side of the upstream layer 120 and the downstream layer 118 are configured to distribute body fluid. The hydrophobic side may also be referred to as a wicking side, wicking surface, distribution surface, distribution side, or fluid distribution surface. The hydrophobic side may be a smooth distribution surface configured to move fluid through the upstream layer 120 and the downstream layer 118 along a grain of the upstream layer 120 and the downstream layer 118, respectively, distributing fluid throughout the upstream layer 120 and the downstream layer 118. The hydrophilic side may be configured to acquire fluid from the hydrophobic side to aid in fluid movement into the absorbent member 116. The hydrophilic side may also be referred to as a fluid acquisition surface, fluid acquisition side, hydrophilic acquisition surface, or hydrophilic acquisition side. The hydrophilic side may be a fibrous surface and be configured to draw fluid into the upstream layer 120 and the downstream layer 118.

In some exemplary embodiments, the hydrophobic side may be disposed adjacent to the absorbent member 116. In other exemplary embodiments, the hydrophilic side may be disposed adjacent to the absorbent member 116. In still other exemplary embodiments, the downstream layer 118 may have the hydrophilic side disposed adjacent to the absorbent member 116 and the upstream side 120 may have the hydrophobic side adjacent to the absorbent member 116. In yet other exemplary embodiments, the downstream layer 118 may have the hydrophobic side disposed adjacent to the absorbent member 116 and the upstream side 120 may have the hydrophilic side adjacent to the absorbent member 116.

A reduced-pressure therapy system may also include a connector or adapter configured to fluidly couple a tube, such as the tube 108, to a dressing, such as the dressing 104. A connector may include a flange portion that couples to a dressing, and a port portion that fluidly couples to a tube. The flange portion may fluidly couple the connector to the dressing 104, for example, and the port portion may fluidly couple the connector to the reduced pressure source. In this manner, the connector may prevent fluid communication between the sealed therapeutic environment and the ambient environment, while allowing fluid communication between a tissue site and a reduced-pressure source through the dressing. A connector may also include a primary filter disposed within a fluid channel. The primary filter may comprise a hydrophobic material substantially filling the fluid channel through the connector and be adapted to limit passage of liquids through the connector into a tube.

A connector may have an open area, such as a cavity, bounded by a flange portion and fluidly coupled to a port portion. If the connector is disposed on a dressing, the cavity may be aligned with an opening in the drape so that fluid communication may occur between the tissue site and the connector through the aperture. The cavity may provide the primary fluid connection between a tube and a dressing, transitioning fluid flow between a manifold and an internal diameter of the tube.

Often, a manifold may be significantly larger than the diameter of a tube. A connector, and specifically a cavity in the connector, can operate to transition reduced pressure from a tube to a manifold, and transition fluid drawn into the manifold to the tube. Preferably, the fluid transition occurs with as little restriction as possible so that the application of therapeutic reduced pressure is not undesirably terminated. Consequently, reduced pressure supplied to a tissue site should be accommodated by a cavity, and the fluid removed from the tissue site should also be accommodated by the cavity.

For example, a cavity of a connector can channel a large volume of fluid from a tissue site that produces a large amount of fluid into a tube and at a flow rate high enough to avoid loss of reduced pressure. In addition, a cavity may have to accommodate movement of solids from a tissue site into a container, again without causing a loss of reduced pressure at the tissue site. If fluid is retained in a dressing, for example in the container 114, the portion of a cavity in fluid communication with a tissue site must have a sufficient surface area to ensure that the therapeutic reduced pressure can be supplied to the tissue site. A cavity should also be able to accommodate sufficient flow to manage leaks, for example, between the drape 108 and the intact epidermis surrounding the tissue site 102. A cavity can provide these functions with as little restriction to fluid flow between a tube and a tissue site as possible to avoid undesired cessation of the application of reduced-pressure therapy.

As a cavity may be the fluid connection means between a tube and a dressing, the cavity should be sufficiently large to avoid restricting the flow of fluid between a tissue site and a reduced-pressure source. Having a sufficiently sized cavity becomes more imperative where the flow of fluid, both of liquids from a tissue site to a reduced-pressure source and of reduced pressure from the reduced-pressure source to the tissue site is continuous.

To provide an effective transition between a manifold and a tube, a cavity may transition from a relatively large aperture disposed proximate to a manifold to a relatively small lumen of a tube. Such an aperture typically may have a diameter larger than the diameter of a lumen but smaller than the exposed surface area of a manifold. In an exemplary embodiment, an aperture may have a diameter substantially similar to the diameter of an opening formed in a drape that allows a reduced-pressure source to be fluidly coupled to a sealed therapeutic environment. A cavity may have a shape that transitions an aperture to a port portion so that fluid may be encouraged to flow toward a lumen. Some connectors may have a domed-shape cavity, for example, which can extend greater than 5 mm in a vertical direction from a flange portion. In addition, a profile of a cavity may have a sharp change in profile height from a flange portion of a connector to a wall of the connector forming the cavity.

For low acuity systems, a container may be disposed adjacent a tissue site between a manifold and a drape. Flow of fluid past such a container during reduced-pressure therapy may represent a failure of a connector. For example, if a continuous application of reduced pressure is required during therapy, a drape may not be sealed to the undamaged epidermis proximate to a tissue site. In another example, if fluid, including liquid, are moved through a connector during the application of reduced pressure, a filter disposed between the connector and a container may not be retaining fluid in the container. In these situations, the fluid flow rate at the initiation of reduced pressure therapy may be significantly higher than the flow rate once the sealed therapeutic environment may have reached a therapeutic reduced pressure.

A connector may have a profile that presents significant challenges to treating tissue sites located where a patient may rest upon the tissue site, or that may be a weight-bearing tissue site, such as a pressure ulcer on the foot, the back of a leg, a hip, or a buttock area, for example. Relatively tall features of a connector on a dressing may cause discomfort if a patient places weight on a tissue site. The discomfort may be caused in part by a connector being pressed into a tissue site by a patient's weight, for example. The discomfort may also be caused by the application of compression therapy in addition to reduced-pressure therapy, for example, for a patient with venous leg disease. In extreme cases, a patient may experience secondary damage to a tissue site, for example, where the pressure of a connector on the tissue site may cause an ulcer, damage newly formed tissue, or create a pressure sore.

The potential for discomfort or secondary damage may discourage the use of beneficial reduced-pressure therapy if a tissue site is in a weight-bearing location. In other scenarios, a patient may request discontinuation of reduced-pressure therapy because of the discomfort. Consequently, a significant group of patients that could benefit from reduced-pressure therapy may be excluded. For example, in the PUPPS3 Pressure Ulcer Survey in Australia in 2006, 25.2% of pressure ulcers were on the heel, and 24.8% were on the sacrum, both examples of weight-bearing locations. Clinicians and patients were reportedly not inclined to use reduced-pressure therapy in these weight-bearing locations where a connector was expected to be uncomfortable and unconformable.

Generally, connectors have also been designed to resist collapse under reduced-pressure, which can ensure that a cavity continues to provide a transition between a tube and a manifold. In addition, a connector may still have a profile that exhibits sudden sharp changes in height to accommodate a cavity, for example, at locations of the connector where a flange portion transitions to a cavity portion. Thus, these connectors may still cause patient discomfort and potential pressure ulcers due to the sudden sharp changes in profile height and material hardness.

As disclosed herein, the therapy system 100 can overcome these shortcomings and others by providing a connector with a dynamic profile. For example, as illustrated in the exemplary embodiment of FIG. 1, the therapy system 100 may include a connector 122. The connector 122 may be molded such that an open cavity is provided if there is no pressure differential across the connector 122, but the cavity can collapse and assume a lower profile as therapeutic pressure is applied and increases the pressure differential. In more particular exemplary embodiments, the connector 122 may have a wall adapted to change the geometric profile of the connector 122 in response to the application of reduced-pressure. The profile of the connector 122 may also revert back to the original profile if the differential pressure is equalized, such as if therapy is terminated. In general, the connector 122 may have a low profile with a dynamic cavity wall to reduce the risk of patient discomfort or secondary damage.

Figure 2:
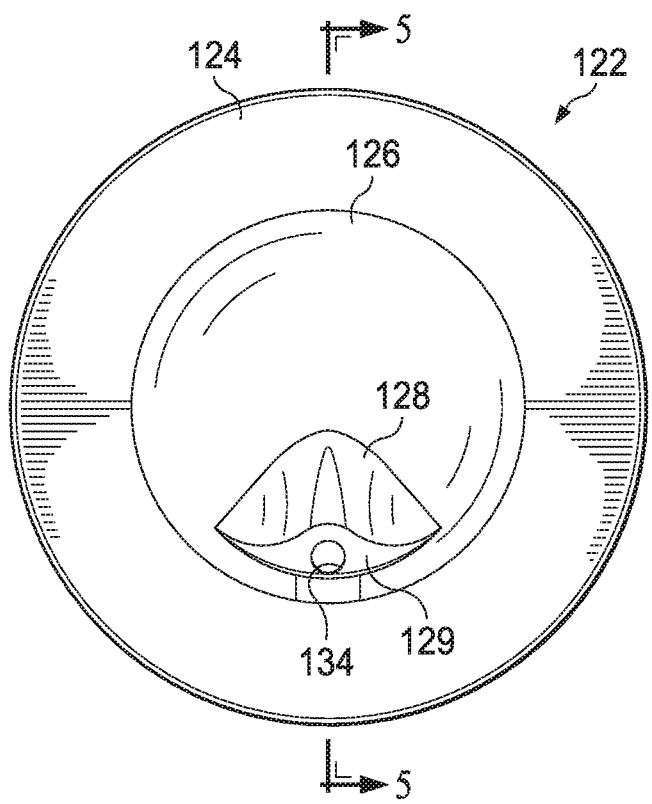
FIG. 2 is a top view of a connector of the reduced-pressure therapy system of FIG. 1.
Figure 3:
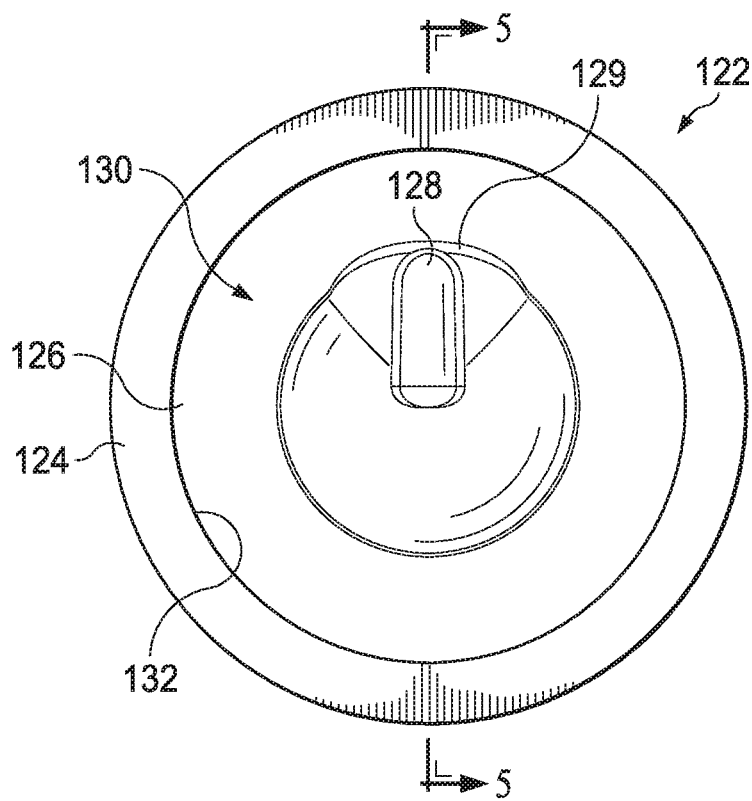
FIG. 3 is a bottom view of the connector of FIG. 2.
Figure 4:
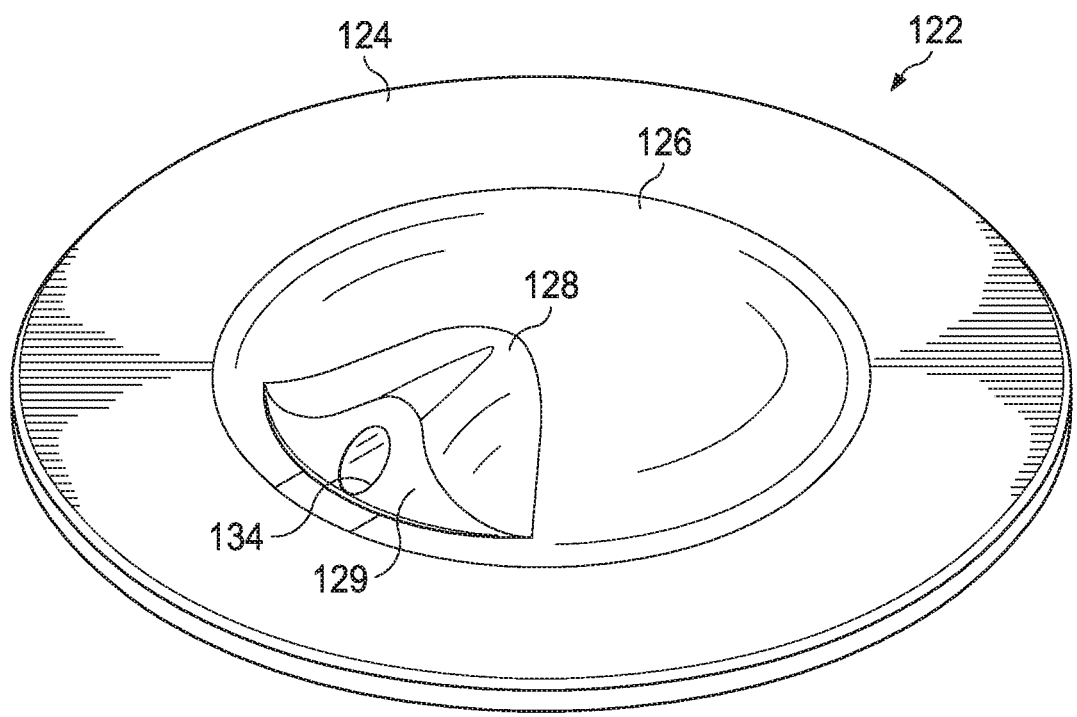
FIG. 4 is a perspective view of the connector of FIG. 2.

FIG. 2 is a top view illustrating additional details that may be associated with some embodiments of the connector 122. The connector 122 may include a base 124, a wall 126, and a conduit port 128. FIG. 3 is a bottom view illustrating additional details that may be associated with some embodiments of the connector 122. The base 124 may couple to the wall 126 as shown in the example embodiments of FIG. 2 and FIG. 3. The wall 126 may include an interior surface that defines a cavity 130. The based 124 may have an aperture 132, and a peripheral portion of the wall 126 may be coupled to the base 124 adjacent to the aperture 132 so that the cavity 130 is in fluid communication with the aperture 132. FIG. 4 is a perspective view illustrating additional details that may be associated with some embodiments of the connector 122. As shown in FIG. 4, the wall 126 may be a generally semi-spherical structure having an exterior surface. The conduit port 128 protrudes from the exterior surface of the wall 126 and may include a lumen 134. The conduit port 128 may be narrower proximate to the apex of the wall 126 and broader proximate to the base 124 so that the conduit port may have a slightly pyramidal shape. Sides of the conduit port 128 may slope to the apex of the wall 126 from a first end 127 to a second end 129 so that the conduit port 128 may protrude from the wall 126 proximate to the base 124. The sides of the conduit port 128 may taper as the sides of the conduit port 128 extend between the base 124 and the apex of the wall 126.

Figure 5:
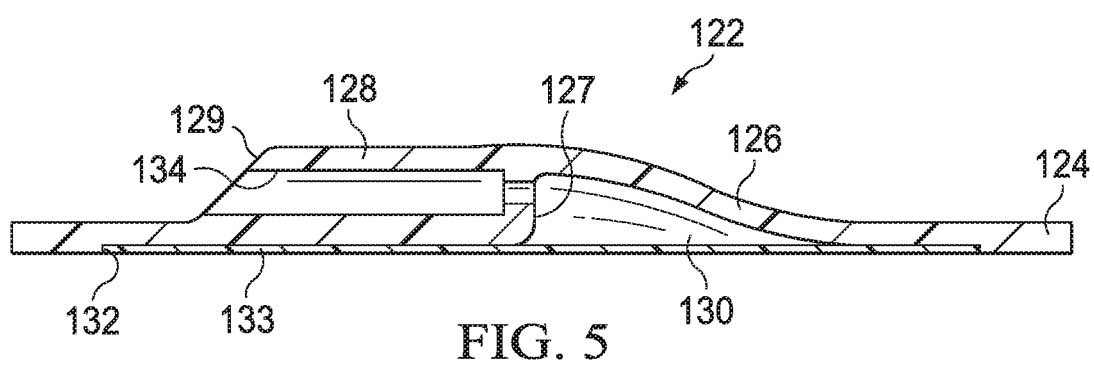
FIG. 5 is a sectional view of the connector taken along line 5-5 of FIG. 2 in a first position.

FIG. 5 is a sectional view illustrating additional details that may be associated with some embodiments of the connector 122. As shown in FIG. 5, the base 124 may be a flange having at least a portion that is substantially planar and adapted to couple to the dressing 104. In some exemplary embodiments, the base 124 may have a diameter of about 42 mm. In other exemplary embodiments, the base 124 may have a larger or smaller diameter. In some exemplary embodiments, the base 124 may have a thickness of about 1.25 mm. In some exemplary embodiments, the base 124 may have a thickness in the range of about 0.60 mm to about 2.00 mm. In still other exemplary embodiments, the thickness of the base 124 may be greater than about 2.00 mm or less than about 0.60 mm. The base 124 may include an adhesive or other attachment device on a lower surface of the base 124 so that the base 124 may be coupled to the drape 110.

The wall 126 may include peripheral portions that can be coupled to the base 124 so that the base 124 extends outwardly away from the wall 126. The wall 126 may have a height relative to an upper surface of the base 124 of about 3 mm. For example, the wall 126 may protrude about 3 mm from the upper surface of the base 124 to an apex of the wall 126. The wall 126 may have a thickness of about 1.25 mm. In some exemplary embodiments, the wall 126 may have a thickness in the range of about 0.60 mm to about 2.00 mm. In still other exemplary embodiments, the thickness of the wall 126 may be greater than about 2.00 mm or less than about 0.60 mm. The thickness of the wall 126 may be substantially the same from the peripheral portions where the wall 126 joins the base 124 to the apex of the wall 126. In other exemplary embodiments, the thickness of the wall 126 may vary from the peripheral portions where the wall 126 joins the base 124 to the apex.

The aperture 132 in the base 124 may permit fluid communication into the cavity 130. The aperture 132 may be located proximate to the peripheral portions of the wall 126 and adjacent to the base 124. In some exemplary embodiments, the aperture 132 may have a diameter of about 34 mm. In other exemplary embodiments, the aperture 132 may have a diameter in the range of about 26 mm to about 34 mm. In still other exemplary embodiments, the aperture 132 may have a diameter greater than about 34 mm and less than about 26 mm. The filter 133 may be disposed within the aperture 132. The filter 133 may be a hydrophobic filter adapted to limit movement of liquid into the cavity 130. The filter 133 may have a thickness less than the thickness of the base 124. In some exemplary embodiments, the filter 133 may be welded to the base 124.

The conduit port 128 may be fluidly coupled to the cavity 130 to provide fluid communication with the cavity 130 through the wall 126. The conduit port 128 may have the first end 127 proximate to a center portion of the cavity 130 and the apex of the wall 126 and the second end 129 that terminates at the wall 126 and proximate to the base 124. The illustrative conduit port 128 may include the lumen 134 extending from the first end 127 to the second end 219 of the conduit port 128 and permits fluid communication with the cavity 130 through the wall 126. For example, the tube 108 may be fluidly coupled to the cavity 130 through the conduit port 128 so that reduced pressure may be supplied to the cavity 130 through the lumen 134 of the conduit port 128. In some exemplary embodiments, the lumen 134 may have a diameter of about 2 mm and tapers from the second end 129 to the first end 127. In other exemplary embodiments, the lumen 134 may have a diameter greater than or less than 2 mm and may not taper.

In some exemplary embodiments, the connector 122 may include one or more channels formed on portions of the inside surfaces of the wall 126 within the cavity 130 extending between the base 124 and the conduit port 128. These channels may direct the flow of fluid and exudates from the tissue site 102 and the manifold 112 to the conduit port 128.

The connector 122 may be made of a semi-rigid material capable of collapsing under a force. In some exemplary embodiments, the connector 122 may be formed of a material having a durometer of about 68 Shore A. In other exemplary embodiments, the connector 122 may have a durometer larger or smaller then 68 Shore A, for example, in the range of about 25 Shore A to about 100 Shore A. In a non-limiting example, the connector 122 may be made from a plasticized polyvinyl chloride (PVC) that is bis(2-ethylhexyl) phthalate (DEHP) free, for example Colorite P/N 6877G-015. In another exemplary embodiment, the connector 122 may be formed of 0.007% plasticized PVC. In still other exemplary embodiments, the connector 122 may be made from polyurethane, cyclic olefin copolymer elastomer, thermoplastic elastomer, poly acrylic, silicone polymer, or polyether block amide copolymer.

The thickness of the wall 126 and the durometer of the wall 126 are selected so that the wall 126 may be a dynamic component of the connector 122. For example, the thickness of the wall 126 and the durometer of the wall 126 are selected so that the wall 126 may have a first position having a first profile as shown in FIG. 5. As shown in FIG. 5, the first position may form the cavity 130 having a first volume that may be adapted to permit a fluid flow rate sufficient to provide the therapeutic reduced pressure at the manifold 112 if the connector 122 is disposed proximate to the dressing 104. The process of reducing pressure within the sealed therapeutic environment may be commonly referred to as "drawing down" a dressing. The first profile may extend vertically from the base 124 then slope horizontally toward the apex of the wall 126 proximate to the conduit port 128.

Figure 6:
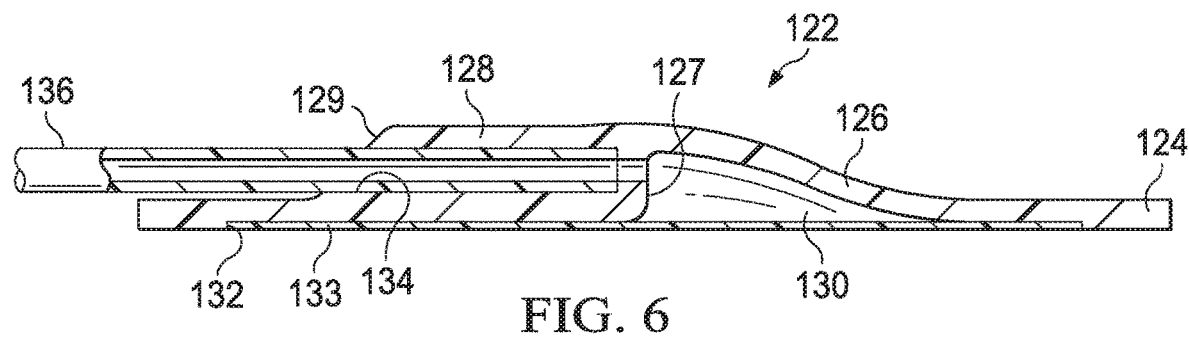
FIG. 6 is a sectional view of the connector having a connector conduit fluidly coupled thereto.

FIG. 6 is a sectional view illustrating additional details that may be associated with some embodiments of the connector 122. As shown in FIG. 6, the connector 122 may include a connector conduit 136. The connector conduit 136 may be a tube similar to the tube 108 having a first end adapted to be inserted into the lumen 134 of the conduit port 128 and a second end adapted to be inserted into a lumen of the tube 108. The connector conduit 136 may be more rigid than the tube 108 to limit bending of the connector conduit 136 proximate to the port 128 and to reduce instances of restriction proximate to the connector 122. In addition, the connector conduit 136 may have a smaller outer diameter than the tube 108. In an exemplary embodiment, the connector conduit 136 may have a diameter of about 2 mm. The diameter of the connector conduit 136 may be selected to reduce patient discomfort if the connector conduit 136 is disposed proximate to a tissue site at a weight-bearing location. In some exemplary embodiments, the diameter of the connector conduit 136 may be about the same as the height of the connector 122 from the top of the base 124 to the apex of the wall 126.

Figure 7:
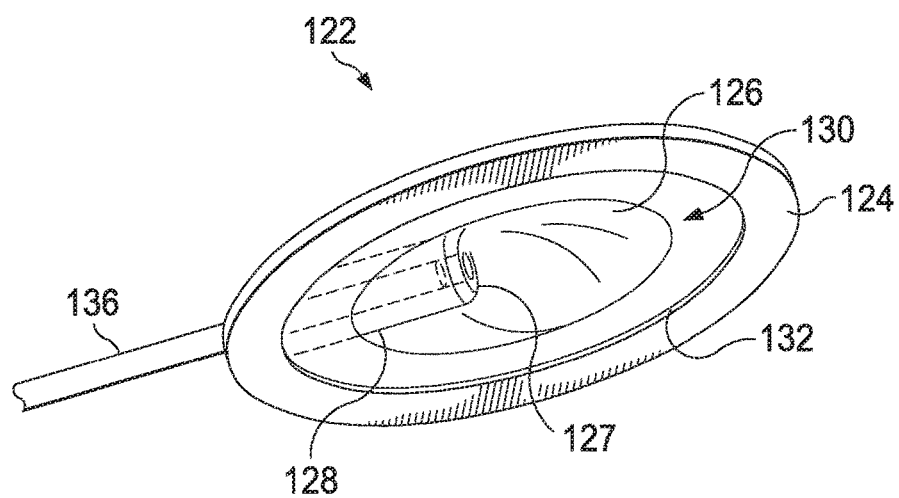
FIG. 7 is another perspective view of the connector of FIG. 2.

FIG. 7 is a perspective view illustrating additional details that may be associated with some embodiments of the connector 122. As shown in FIG. 7, the wall 126 may be in the first position so that the cavity 130 has the first volume that permits fluid flow between a tissue site and a reduced pressure source. The connector 122 provides the cavity 130 having the first volume permitting a first flow rate if a reduced-pressure less than the therapeutic reduced pressure is applied. The first volume may permit flow of fluid and reduced pressure in a relatively unrestricted manner so that the dressing 104 may be drawn down.

Figure 8:
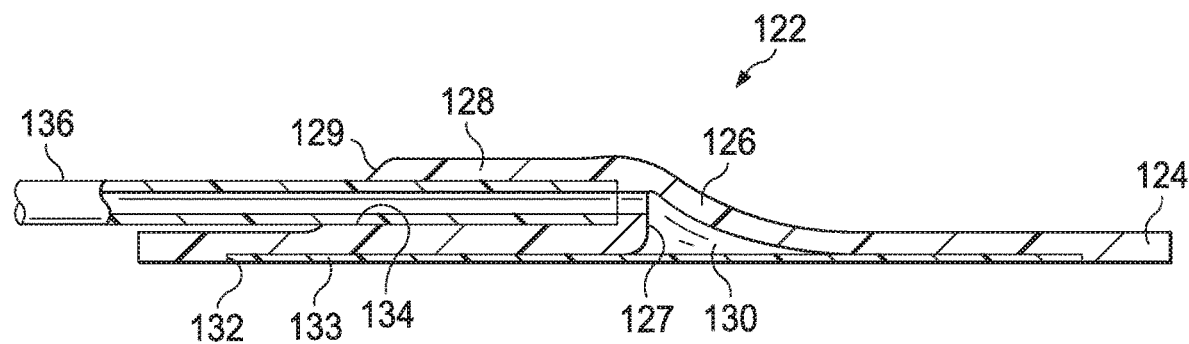
FIG. 8 is a sectional view of the connector of the reduced-pressure therapy system of FIG. 2 in a second position.

FIG. 8 is a sectional view illustrating additional details that may be associated with some embodiments of the connector 122. The wall 126 is shown in a second position having a second profile. Once the dressing is drawn down, as described above, the wall 126 can collapse, at least partially, to the second position. If the dressing is drawn down and the wall 126 at least partially collapses, at least a portion of the wall 126 may be proximate to the aperture 132. In some exemplary embodiments, at least a portion of the interior surface of the wall 126 in the second position may be located in a same horizontal plane as the lower surface of the base 124. Collapse of the wall 126 to the second position reduces the volume of the cavity 130. The second profile of the wall 126 may extend horizontally from the base 124, sloping toward the conduit port 128. Generally, if the wall 126 is in the second position a substantial portion of the profile of the connector 122 may have a height the same as the thickness of the wall 126. In some exemplary embodiments, the profile slopes from a height of about 1.25 mm to a height of about 4.25 mm. In some exemplary embodiments, the fluid connection between the manifold 112 and the reduced-pressure source 106 may be severed when the wall 126 is in the second position.

The durometer and the thickness of the wall 126 may be selected so that the wall 126 collapses from the first position to the second position at desired levels of therapeutic reduced pressure. In an exemplary embodiment, the durometer may be about 68 Shore A and the thickness of the wall 126 may be about 1.25 mm. In another exemplary embodiment, the connector 122 may be formed of a 0.007% plasticized PVC; thus, the durometer of the connector 122 may be held constant. The thickness of the wall 126 may then be selected based on the desired profile height reduction under a therapeutic reduced pressure, for example 125 mmHg. In some exemplary embodiments, if a profile height reduction between the first position and the second position of about 5.25 mm is desired, the thickness of the wall 126 may be about 0.6 mm. In other exemplary embodiments, if a profile height reduction between the first position and the second position of about 1.25 mm is desired, the thickness of the wall 126 may be about 1.25 mm. In still other exemplary embodiments, if a profile height reduction between the first position and the second position of about 0.75 mm is desired, the thickness of the wall 126 may be about 1.85 mm.

Figure 9:
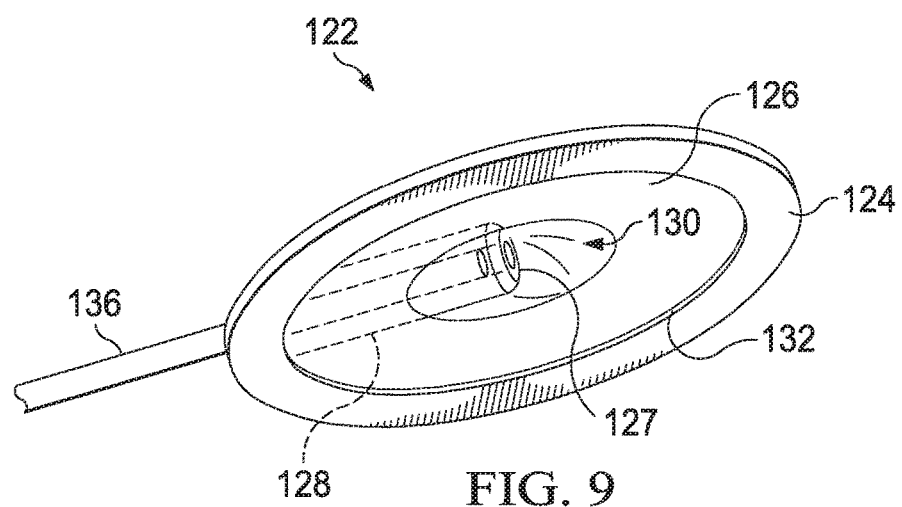
FIG. 9 is a perspective view of the connector of FIG. 4.

FIG. 9 is a perspective view illustrating additional details that may be associated with some embodiments of the connector 122. As shown in FIG. 9, the wall 126 may have collapsed to the second position so that the cavity 130 has the second volume, substantially reducing the profile of the connector 122. If the dressing 104 has been drawn down and the sealed therapeutic environment has reached the therapeutic reduced pressure, the wall 126 may collapse to the second position having the second profile, reducing the volume of the cavity 130. If the therapeutic reduced pressure has been reached in the sealed therapeutic environment, the flow rate of fluid through the connector 122 can significantly decrease; consequently, the reduced volume of the cavity 130 with the wall 126 in the second position may not restrict fluid flow. The connector 122 may have a lower profile than conventional connectors, while permitting unrestricted fluid communication during the application of reduced pressure. In addition, the connector 122 may have a profile that reduces sudden changes in profile elevation, decreasing discomfort for a patient. If the application of reduced pressure ceases, or there is a need to supply additional reduced pressure, the connector 122 may return to the first position of FIG. 5, FIG. 6, and FIG. 7. For example, if the amount of reduced pressure supplied to the connector 122 decreases, or if a leaking drape 110 raises the absolute pressure in the sealed therapeutic environment, the wall 126 may expand to the first position. This expansion returns the connector 122 to the first profile to provide a large volume cavity 130 for the unrestricted flow of reduced pressure. The supply of reduced pressure may then be increased to re-pressurize the sealed therapeutic environment. In some exemplary embodiments, the wall 126 may be in the second position during approximately 90% of its use.

In some exemplary embodiments, the connector 122 may provide an indication that the therapeutic reduced pressure has been reached. For example, as the thickness and the durometer of the wall 126 may be selected so that the wall 126 collapses at a known therapeutic reduced pressure, the connector 122 may be visually monitored during the draw-down process. An operator or user can observe that the therapeutic reduced pressure has been reached by the collapse of the wall 126. Similarly, the wall 126 may be visually monitored to determine if the wall 126 is in the first position or the second position to determine whether the tissue site 102 is being provided with therapeutic reduced pressure.

In other exemplary embodiments, a pressure sensor may be included in the connector 122 to measure the pressure provided to the cavity 130. In some exemplary embodiments, the pressure sensor may include a pressure sensing lumen routed through the conduit port 128 and fluidly coupled to the reduced pressure source 106.

In some exemplary embodiments, the connector 122 may be used with instillation therapy. For example, the connector 122 may permit an unrestricted flow of fluid during the application of instilling fluid, an unrestricted flow of fluid during withdrawal of the instilling fluid, and then a restricted flow following removal of all instilling fluid.

The systems and methods described herein may provide significant advantages, some of which have already been mentioned. For example, the therapy system 100 may be particularly advantageous for low-acuity wounds, which typically have sustained fluid flow at the beginning of therapy when a dressing is evacuated. Thereafter, only minimal fluid flow may be anticipated for low-acuity wounds. Thus, a low-acuity wound typically may have two different and contradictory flow conditions during the course of therapy. Initially, a low-acuity wound may need a connector that may be relatively large and open to flow during draw-down, but may benefit significantly from a connector with a reduced profile when flow is reduced after draw down. The therapy system 100 provides a connector with a dynamic profile that can satisfy both of these flow conditions, and may be used on a tissue site at weight-bearing locations while reducing or substantially eliminating discomfort and secondary damage to the tissue site. The operating principle of the therapy system 100 may be extended to connectors which provide active fluid removal such as with connectors configured to have a canister for collecting fluid between the connector and the reduced pressure source. The connector may be fluidly coupled to the manifold and the amount of profile height reduction may be selected to maintain a fluid flow when the pad collapses. Similarly, the connector durometer and thickness may be selected to allow for use with instillation systems to both supply and withdraw instilling fluid.

It should be apparent from the foregoing that an invention having significant advantages has been provided. Any feature that is described in connection to any one exemplary embodiment may also be applicable to any other exemplary embodiment, and the benefits and advantages described above may relate to one exemplary embodiment or may relate to several exemplary embodiments. While shown in only a few forms, the systems and methods illustrated are susceptible to various changes and modifications without departing from the scope of the claims.

We claim:

1. A system for treating a tissue site with reduced pressure, the system comprising:
    a manifold adapted to be placed proximate to the tissue site;
    a sealing member adapted to cover the manifold to form a sealed space;
    a reduced-pressure source adapted to supply reduced pressure to the manifold;
    a connector comprising:
        a wall forming a cavity adapted to fluidly couple to the manifold through the sealing member, the wall adapted to transition between a first position providing a first volumetric flow rate through the cavity at a flow velocity and a second position providing a second volumetric flow rate through the cavity while maintaining the flow velocity in response to a change in a supply of reduced pressure,
        a conduit port adapted to fluidly couple the cavity to reduced-pressure source, and
        a base extending from a peripheral portion of the wall and adapted to be coupled to the sealing member.

2. The system of claim 1, wherein the wall has a thickness in a range of about 0.60 mm to about 2.00 mm.

3. The system of claim 1, wherein the wall has a thickness of about 1.25 mm.

4. The system of claim 1, wherein the wall comprises a polymer having a durometer in a range of about 25 Shore A to about 100 Shore A.

5. The system of claim 1, wherein the wall comprises a polymer having a durometer of about 68 Shore A.

6. The system of claim 1, wherein the wall comprises a polymer having a durometer in a range of about 25 Shore A to about 100 Shore A and a thickness in a range of about 0.60 mm to about 2.00 mm.

7. The system of claim 1, wherein the wall comprises a polymer having a durometer and a thickness so that the wall is adapted to collapse from the first position to the second position.

8. The system of claim 1, wherein the wall has a sloping profile in the second position.

9. The system of claim 1, wherein the cavity has a first volume when the wall is in the first position and a second volume when the wall is in the second position.

10. The system of claim 1, wherein the cavity has a first volume when the wall is in the first position, a second volume when the wall is in the second position, and the first volume is greater than the second volume.

11. The system of claim 1, wherein the cavity has a height from a top of the base to a top of the wall of about 3 mm.

12. The system of claim 1, wherein the base has a diameter of about 26 mm.

13. The system of claim 1, further comprising a conduit fluidly coupled to the conduit port and the reduced-pressure source.

14. The system of claim 1, further comprising a conduit fluidly coupled to the conduit port, the conduit having a diameter of about 2 mm.

15. The system of claim 1, further comprising a conduit having a first end inserted into the conduit port and a second end adapted to be inserted into a lumen of a tube fluidly coupling the reduced-pressure source to the connector.

16. The system of claim 1, further comprising a conduit having a diameter of about 2 mm, a first end inserted into the conduit port, and a second end adapted to be inserted into a lumen of a tube fluidly coupling the reduced-pressure source to the connector.

17. The system of claim 1, further comprising an adhesive coupled to the base and adapted to couple the base to the sealing member, the adhesive adapted to create a fluid seal between the base and the sealing member.

18. The system of claim 1, further comprising an instillation module adapted to be coupled to the connector to supply instillation fluid to the tissue site through the cavity.

19. The system of claim 1, wherein the wall and the base comprise polyvinyl chloride.

20. A method of treating a tissue site with reduced pressure, the method comprising:
    disposing a manifold proximate to the tissue site;
    securing a sealing member over the manifold and a portion of intact epidermis to form a sealed space, the sealing member having an opening formed therein;
    coupling a connector to the sealing member proximate to the opening, the connector having a dynamic cavity wall;
    fluidly coupling a reduced-pressure source to the connector to supply reduced pressure to the manifold;
    supplying reduced pressure to the manifold through the connector; and
    collapsing at least a portion of the dynamic cavity wall from a first position providing a first volumetric flow rate through a cavity at a flow velocity to a second position providing a second volumetric flow rate through the cavity while maintaining the flow velocity when a therapeutic reduced pressure is reached in the sealed space.

21. The method of claim 20, wherein supplying reduced pressure to the manifold through the connector further comprises supplying reduced pressure through a first volume of the cavity when the wall is in the first position and a second volume when the wall is in the second position.

22. The method of claim 20, wherein supplying reduced pressure to the manifold through the connector further comprises supplying reduced pressure through a first volume of the cavity when the wall is in the first position and a second volume when the wall is in the second position, and the first volume is greater than the second volume.

23. The method of claim 20, wherein fluidly coupling a reduced-pressure source to the connector to supply reduced pressure to the manifold further comprises fluidly coupling a conduit to a conduit port.

24. The method of claim 20, wherein fluidly coupling a reduced-pressure source to the connector to supply reduced pressure to the manifold further comprises fluidly coupling a conduit having a diameter of about 2mm to a conduit port.

25. The method of claim 20, wherein fluidly coupling a reduced-pressure source to the connector to supply reduced pressure to the manifold further comprises fluidly coupling a conduit to a conduit port, the conduit having a first end adapted to be inserted into the conduit port and a second end adapted to be inserted into a larger conduit.

26. The method of claim 20, wherein fluidly coupling a reduced-pressure source to the connector to supply reduced pressure to the manifold further comprises fluidly coupling a conduit having a diameter of about 2 mm to a conduit port, the conduit having a first end adapted to be inserted into the conduit port, and a second end adapted to be inserted into a larger conduit.

27. The method of claim 20, wherein coupling a connector to the sealing member further comprises coupling an adhesive to a base and to a dressing, the adhesive adapted to create a fluid seal between the base and the dressing.

* * * * *